(12) United States Patent
Sigal et al.

(10) Patent No.: US 9,109,030 B1
(45) Date of Patent: *Aug. 18, 2015

(54) EPSIGAM FUSION PROTEIN

(71) Applicant: Tunitas Therapeutics, Inc., San Francisco, CA (US)

(72) Inventors: Nolan Sigal, Los Altos, CA (US); Gizette Sperinde, El Granada, CA (US)

(73) Assignee: TUNITAS THERAPEUTICS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,003

(22) Filed: Jan. 9, 2015

Related U.S. Application Data (63) Continuation of application No. 14/243,750, filed on Apr. 2, 2014, now Pat. No. 8,961,992.

(51) Int. Cl.
*C07K 16/28* (2006.01)
*A61K 39/395* (2006.01)

(52) U.S. Cl.
CPC ......... *C07K 16/2851* (2013.01); *C07K 2319/30* (2013.01); *Y10S 424/805* (2013.01); *Y10S 424/81* (2013.01)

(58) Field of Classification Search
None
See application file for complete search history.

(56) References Cited

U.S. PATENT DOCUMENTS

| | | | |
|---|---|---|---|
| 3,187,748 | A | 6/1965 | Mitchell et al. |
| 3,656,070 | A | 4/1972 | Monaghan et al. |
| 3,658,059 | A | 4/1972 | Steil |
| 3,814,297 | A | 6/1974 | Warren |
| 3,826,413 | A | 7/1974 | Warren |
| 4,208,479 | A | 6/1980 | Zuk et al. |
| 4,527,769 | A | 7/1985 | Stogner et al. |
| 4,592,348 | A | 6/1986 | Waters, IV et al. |
| 4,648,393 | A | 3/1987 | Landis et al. |
| 4,677,975 | A | 7/1987 | Edgar et al. |
| 4,683,195 | A | 7/1987 | Mullis et al. |
| 4,790,305 | A | 12/1988 | Zoltan et al. |
| 4,803,978 | A | 2/1989 | Johnson, IV et al. |
| 4,896,832 | A | 1/1990 | Howlett |
| 4,922,901 | A | 5/1990 | Brooks et al. |
| 4,926,852 | A | 5/1990 | Zoltan et al. |
| 4,943,529 | A | 7/1990 | Van Den Berg et al. |
| 5,329,028 | A | 7/1994 | Ashkenazi et al. |
| 7,265,208 | B2 | 9/2007 | Saxon et al. |
| 7,488,804 | B2 * | 2/2009 | Saxon et al. ............ 530/387.3 |
| 7,544,783 | B2 * | 6/2009 | Chen et al. ............. 530/387.3 |
| 7,566,456 | B2 | 7/2009 | Chen |
| 2003/0082190 | A1 | 5/2003 | Saxon et al. |
| 2004/0198961 | A1 * | 10/2004 | An et al. ................. 530/391.1 |

FOREIGN PATENT DOCUMENTS

| | | |
|---|---|---|
| EP | 0183070 | 6/1986 |
| WO | WO92/09300 | 6/1992 |
| WO | WO96/22024 | 7/1996 |
| WO | WO98/09344 | 3/1998 |
| WO | WO00/29431 | 5/2000 |
| WO | WO02/088317 | 11/2002 |
| WO | WO02/102320 | 12/2002 |

OTHER PUBLICATIONS

Adamczewski. The High-Affinity Receptor for Immunoglobulin E. Chemical Immun. 59:173-190 (1994).
Adelman et al. In vitro deletional mutagenesis for bacterial production of the 20,000-dalton form of human pituitary growth hormone. DNA 2:183-193 (1983).
Altschul et al. Gapped BLAST and PSI-BLAST: A New generation of protein database search programs. Nucleic Acids Research 25:3389-3402 (1997).
Ashman et al. Fc receptor off-signal in the B cell involves apoptosis. J. Immunol. 157:5-11 (1996).
Ballance et al. Transformation of *Aspergillus nidulans* by the orotidine-5'phosphate decarboxylase gene of *Neurospora crassa*. Biochem. Biophys. Res. Commun 112:284-289 (1983).
Barnes. Anti-IgE antibody therapy for asthma. The New England Journal of Medicine. 341:2006-2008 (1999).
Barany et al. The Peptide: Analysis Synthesis, Biology, editors E. Gross and J. Meienhofer. Academic Press, New York (1980) Chapter 1(vol. 2):3-254.
Beach et al. High-frequency transformation of the fission yeast *Schizosaccharomyces pombe*. Nature 290:140-142 (1981).
Beasley et al. Prevalence and etiology of asthma. J. Allergy Clin. Immunol. 105:466-472 (2000).
Benoist et al. A revival of the B cell paradigm for rheumatoid arthritis pathogenesis? Arthritis Res. 2:90-94 (2000).
Blom et al. Phenotypic characterization of KU812, a cell line identified as an immature human basophilic leukocyte. Eur J Immunol. 22:2025-32 (1992).
Blom et al. Characterization of a human basophil-like cell line (LAMA-84). Scand J Immunol., 44:54-61 (1996).
Blondel et al. Engineering the quaternary structure of an exported protein with a leucine zipper. Protein Engineering. 4:457-461 (1991).
Borel et al. A novel technique to link either proteins or peptides to gammaglobulin to construct tolerogens. J of Immunological Methods. 126(2):159-168 (1990).
Botstein et al. Strategies and applications of in vitro mutagenesis. Science 229:1193-1201 (1985).
Brake et al. α-factor-directed synthesis and secretion of mature foreign proteins in *Saccharomyces cerevisiae*. Proc. Natl. Acad. Sci. 81:4642-4646 (1984).
Cambier et al. Inhibitory receptors abound? Proc. Natl. Acad. Sci. 94:5993-5995 (1997).
Carter et al. Improved oligonucleotide site-directed mutagenesis using M13 vectors. Nucl. Acids Res. 13:4331-4343 (1986).
Chan et al. Regulation of the immune response. V. An analysis of the function of the Fc portion of antibody in suppression of an immune response with respect to interaction with components of the lymphoid system. Immunology 21:967-981 (1971).

(Continued)

*Primary Examiner* — Michael Szperka
(74) *Attorney, Agent, or Firm* — Wilson Sonsini Goodrich & Rosati (57) ABSTRACT

Epsi-gam provides a novel fusion protein with the ability to cross-link either of the FcεRI or FcεRII cell surface receptors with an FcγRIIb cell surface receptor in order to block IgE-mediated biological responses.

15 Claims, 6 Drawing Sheets

(56) References Cited

OTHER PUBLICATIONS

Daeron et al. The same tyrosine-based inhibition motif, in the intracytoplasmic domain of Fc gamma RIIB, regulates negatively BCR-, TCR-, and FcR-dependent cell activation. Immunity 3:635-646 (1995).
Daeron et al. Regulation of high-affinity IgE receptor-mediated mast cell activation by murine low-affinity IgG receptors. J. Clin. Invest., 95:577-85 (1995).
Daeron et al. Fc Receptor Biology. Annu. Rev. Immunol. 5:203-234 (1997).
Delespesse et al. The low-affinity receptor for IgE. Immunol. Rev. 125:77-97 (1992).
Dombrowicz et al. Anaphylaxis mediated through a humanized high affinity IgE receptor. Journal of Immunology 157:1645-1651 (1996).
Ellison et al. Nucleotide sequence of a human immunoglobulin Cγ4 gene. DNA 1:11-18 (1982).
Ellison et al. The nucleotide sequence of a human immunoglobulin Cγ1 gene. Nucl. Acid Res.10:4071-4079 (1982).
Ellison et al. Linkage and sequence homology of two human immunoglobulin γ heavy chain constant region genes. Proc. Nat. Acad. Sci. 79:1984-1988 (1982).
EP10010375.3 Extended Search Report dated May 2, 2011.
Fiebiger et al. Serum IgG autoantibodies directed against the α chain of FcεRI: a selective marker and pathogenetic factor for a distinct subset of chronic urticaria patients? J. Clin. Invest. 96:2606-2612 (1995).
Fiebiger et al. Anti-FcεRIα autoantibodies in autoimmune-mediated disorders. Identification of a structure-function relationship. J. Clin. Invest. 101:243-251 (1998).
Fridman. Fc receptors and immunoglobulin binding factors. FASEB J. 5(12):2684-90 (1991).
Gollnick et al. Isolation, characterization, and expression of cDNA clones encoding the mouse Fc receptor for IgE (FcεRII)1. J. Immunol. 144:1974-82 (1990).
Graham et al. Characteristics of a human cell line transformed by DNA from human adenovirus type 5. J. Gen. Virol. 36:59-72 (1977).
Hellman. Characterization of four novel ε chain mRNA and a comparative analysis of genes for immunoglobulin E in rodents and man. Eur. J. Immunol. 23:159-167 (1992).
Helm et al. Identification of the High Affinity Receptor Binding Region in Human Immunoglobulin E. J. Cell Biol. 271(13):7494-7500 (1996).
Hide et al. Autoantibodies Against the High-Affinity IgE Receptor As a Cause of Histamine Release in Chronic Urticaria. N. Engl. J. Med. 328:1599-1604 (1993).
JI. Bifunctional Reagents. Meth. Enzymol. 91:580-609 (1983).
Kaplan. Urticaria and Angioedema, In: Inflammation: Basic Principles and Clinical Correlates (Galliin and Snyderman eds.), 3rd Edition, Lippincott & Wilkins, Philadelphia, 1999, Chapter 57:915-928.
Kelly et al. Transformation of *Aspergillus niger* by the amdS gene of *Aspergillus nidulans*. EMBO J. 4:475-479 (1985).
Kepley et al. Negative regulation of FcεRI signaling by FcγRII costimulation in human blood basophils. J of Allergy and Clinical Immunology. 106():337-348 (2000).
Kikutani et al. Molecular structure of human lymphocyte receptor for immunoglobulin E. Cell 47:657-665 (1986).
Kinet. The high-affinity IgE receptor (FcεRI): from physiology to pathology. Annu. Rev. Immunol. 17:931-972 (1999).
Kondo et al. Cloning of cDNAs for new Subtypes of Murine Low-Affinity Fc Receptor for IgE(FcεRII/CD23). Int. Arch. Allergy Immunol. 105:38-48 (1994).
Krawinkel et al. Comparison of the hinge-coding segments in human immunoglobuulin gamma heavy chain genes and the linkage of the gamma 2 and gamma 4 subclass genes. EMBO J. 1:403-407 (1982).
Kunkel et al. Rapid and Efficient site-Specific Mutagenesis without Phenotypic Selection. Methods Enzymol. 154:367-382 (1987).
Landschulz et al. The leucine zipper: a hypothetical structure common to a new class of DNA binding proteins. Science 240:1759-1764 (1988).
Liu et al. Blockade of peanut allergy with a novel Ara h 2-Fcγ fusion protein in mice. J. Allergy Clin Immunol. 131(1):213-221 (2013).
Ludin et al. Cloning and expression of the cDNA coding for a human lymphocyte IgE receptor. EMBO J. 6:109-114 (1987).
Ma et al. A survey on the management of pollen-food allergy syndrome in allergy practices. J Allergy Clin. Immunol. 112:784-8 (2003).
Malbec et al. Negative regulation of hematopoietic cell activation and proliferation by FcγRIIB. Curr. Top. Microbiol. Immunol. 244:13-27 (1999).
Max et al. Duplication and deletion in the human immunoglobulin ε genes. Cell 29:691-699 (1982).
McKnight. Molecular zippers in gene regulation. Scientific American 264:54-64 (1991).
Metcalfe et al. Mast Cells. Physiol. Rev. 77:1033-1079 (1997).
O'Shea et al. Evidence that the leucine zipper is a coiled coil. Science 243:538-542 (1989).
Ott et al. Activating and inhibitory signaling in mast cells: new opportunities for therapeutic intervention? J. Allergy Clin. Immunol. 106(3):429-440 (2000).
Peat et al. Reversing the trend: reducing the prevalence of asthma. J. Allergy Clin. Immunol. 103:1-10 (1999).
Peng et al. A new isoform of human membrane-bound IgE. J. Immunol. 148:129-136 (1992).
Phillips et al. Cross-linking of B lymphocyte Fcγ receptors and membrane immunoglobulin inhibits anti-immunoglobulin-induced blastogenesis.J. Immunol., 132:627-632 (1984).
Presta et al. The binding site on human immunoglobulin E for its high affinity receptor. J. Biol. Chem., 269:26368-26373 (1994).
Rattan et al. Protein synthesis, posttranslational modifications, and aging. Ann. N.Y Acad. Sci. 663:48-62 (1992).
Roitt et al. Hypersensitivity—Type 1. Chapter 23. Immunology, Fifth Edition, pp. 302-317 (1998).
Saxon et al. Genetically engineered negative signaling molecules in the immunomodulation of allergic diseases. Current Opinion in Allergy & Clinical Immunology 4:563-568 (2004).
Saxon et al Inhibition of human IgE production via FcεR-II stimulation results from a decrease in the mRNA for secreted but not membrane ε H chains. J. Immunol., 147:4000-4006 (1991).
Schmidt-Dorr et al. Construction, purification, and characterization of a hybrid protein comprising the DNA binding domain of the LexA repressor and the Jun leucine zipper: a circular dichroism and mutagenesis study. Biochemistry 30:9657-9664 (1991).
Seifter et al. Analysis for protein modifications and nonprotein cofactors. Meth. Enzymol. 182:626-646 (1990).
Shields et al. High resolution mapping of the binding site on human IgG1 for Fc γRI, FcγRII, FcγRIII, and FcRn and design of IgG1 variants with improved binding to the Fc γ R. J Biol. Chem., 276:6591-6604 (2001).
Sreekrishna et al. High level expression of heterologous proteins in methylotrophic yeast *Pichia pastoris*. J. Basic Microbiol. 28:265-278 (1988).
Takahashi et al. Structure of human immunoglobulin gamma genes: implications for evolution of a gene family. Cell 29:671-679 (1982).
Terada et al. A chimeric human-cat Fcγ-Fel d1 fusion protein inhibits systemic, pulminary, and cutaneous allergic reactivity to intratracheal challenge in mice sensitized to Fel dl, the major cat allergen. Clinical Immunology. 120(1):45-56 (2006).
Tunon De Lara. Immunoglobulins E and inflammatory cells. Rev. Mal. Respir. 13(1):27-36 (1996).
Urlaub et al. Isolation of Chinese hamster cell mutants deficient in dihydrofolate reductase activity. Proc. Natl. Acad. Sci. 77:4216-4220 (1980).
Wang et al. Parenteral Formulations of Proteins and Peptides: Stability and Stablizers. Journal of Parenteral Science and Technology 42(Supp. 1988)s2-s26 (1998).
Watson et al. Molecular cloning and sequencing of the low-affinity IgE receptor (CD23) for horse and cattle. Vet. Immunol. Immunopathol. 73:323-329 (2000).
Wells et al. Cassette mutagenesis: an efficient method for generation of multiple mutations at defined sites. Gene 34:315-323 (1985).

(56) References Cited

OTHER PUBLICATIONS

Wells et al. Importance of Hydrogen-Bond Formation in Stabilizing the Transition State of Subtilisin. Philos. Trans. R. Soc. London SerA, 317:415-423 (1986).

Wetmur et al. Kinetics of Renaturation of DNA. J. Mol. Biol. 31:349-370 (1966).

Wetmur et al. DNA Probes: Applications of the Principles of Nucleic Acid Hybridization. Critical Reviews in Biochemistry and Molecular Biology 26(34):227-259 (1991).

Wines et al. The IgG Fc contains distinct Fc receptor (FcR) binding sites: the leukocyte receptors FcγRI and FcγRIIa bind to a region in the Fc distinct from that recognized by neonatal FcR and protein A. J. Immunol. 164(10):5313-5318 (2000).

Wold. Posttranslational Protein Modifications: Perspectives and Prospects. Posttranslational Covalent Modification of Proteins, Johnson, B. C., ed., Academic Press, New York, pp. 1-12, (1981).

Yodoi et al. Low affinity IgE receptors: regulation and functional roles in cell activation. Ciba Found. Symp. 147:133-148 (1989).

Zhang et al. Inhibition of allergen-specific IgE reactivity by a human Ig Fcγ-Fcε bifunctional fusion protein. J. Allergy Clin. Imm. 114:321-327 (2004).

Zhang et al. Two unusual forms of human immunoglobulin E encoded by alternative RNA splicing of epsilon heavy chain membrane exons. J. Exp. Med. 176:233-243 (1992).

Zhang et al. Chimeric human fcγ-allergen fusion proteins in the prevention of allergy. Immunol Allergy Clin N AM. 27:93-103 (2007).

Zhu et al. A novel human immunoglobulin Fcγ-Fcε bifunctional fusion protein inhibits FcεRI-mediated degranulation. Nat Med 8:518-521 (2002).

Zhu et al. A chimeric human-cat fusion protein blocks cat-induced allergy. Nat Med 11(4):446-449 (2005).

Zoller et al. Oligonucleotide-directed mutagenesis: a simple method using two oligonucleotide primers and a single-stranded DNA template. DNA 3:479-488 (1984).

Zoller et al. Oligonucleotide-directed mutagenesis of DNA fragments cloned into M13 vectors. Methods Enzymol. 100:468-500 (1983).

Zoller et al. Oligonucleotide-directed mutagenesis using M13-derived vectors: an efficient and general procedure for the production of point mutations in any fragment of DNA. Nucl. Acids Res. 10:6487-6500 (1987).

\* cited by examiner

Figure 1

| Construct | Total Protein (mg/L) | Monomer (%) | Aggregate (%) | Final Titer (mg/L) |
|---|---|---|---|---|
| epsi-gam | 1893 | 94 | 6 | 1779 |
| E2G | 0.085 | N/A | Very High | N/A |
| GE2 | 162.4 | 71.9 | 28.1 | 117 |
| GE2 -lys | 6 | 73. | 26.5 | 63 |
| GE2 -Hinge | 166.1 | 70.6 | 29.4 | 117 |

Phe Thr Pro Pro Thr Val Lys Ile Leu Gln Ser Ser Cys Asp Gly Gly Gly His Phe Pro
Pro Thr Ile Gln Leu Leu Cys Leu Val Ser Gly Tyr Thr Pro Gly Thr Ile Asn Ile Thr
Trp Leu Glu Asp Gly Gln Val Met Asp Val Asp Leu Ser Thr Ala Ser Thr Thr Gln Glu
Gly Glu Leu Ala Ser Thr Gln Ser Glu Leu Thr Leu Ser Gln Lys His Trp Leu Ser Asp
Arg Thr Tyr Thr Cys Gln Val Thr Tyr Gln Gly His Thr Phe Glu Asp Ser Thr Lys Lys
Cys Ala Asp Ser Asn Pro Arg Gly Val Ser Ala Tyr Leu Ser Arg Pro Ser Pro Phe Asp
Leu Phe Ile Arg Lys Ser Pro Thr Ile Thr Cys Leu Val Val Asp Leu Ala Pro Ser Lys
Gly Thr Val Asn Leu Thr Trp Ser Arg Ala Ser Gly Lys Pro Val Asn His Ser Thr Arg
Lys Glu Glu Lys Gln Arg Asn Gly Thr Leu Thr Val Thr Ser Thr Leu Pro Val Gly Thr
Arg Asp Trp Ile Glu Gly Glu Thr Tyr Gln Cys Arg Val Thr His Pro His Leu Pro Arg
Ala Leu Met Arg Ser Thr Thr Lys Thr Ser Gly Pro Arg Ala Ala Pro Glu Val Tyr Ala
Phe Ala Thr Pro Glu Trp Pro Gly Ser Arg Asp Lys Arg Thr Leu Ala Cys Leu Ile Gln
Asn Phe Met Pro Glu Asp Ile Ser Val Gln Trp Leu His Asn Glu Val Gln Leu Pro Asp
Ala Arg His Ser Thr Thr Gln Pro Arg Lys Thr Lys Gly Ser Gly Phe Phe Val Phe Ser
Arg Leu Glu Val Thr Arg Ala Glu Trp Glu Gln Lys Asp Glu Phe Ile Cys Arg Ala Val
His Glu Ala Ala Ser Pro Ser Gln Thr Val Gln Arg Ala Val Ser Val Asn Pro Gly Lys
Glu Pro Lys Ser Cys Asp Lys Thr His Thr Cys Pro Pro Cys Pro Ala Pro Glu Leu Leu
Gly Gly Pro Ser Val Phe Leu Phe Pro Pro Lys Pro Lys Asp Thr Leu Met Ile Ser Arg
Thr Pro Glu Val Thr Cys Val Val Val Asp Val Ser His Glu Asp Pro Glu Val Lys Phe
Asn Trp Tyr Val Asp Gly Val Glu Val His Asn Ala Lys Thr Lys Pro Arg Glu Glu Gln
Tyr Asn Ser Thr Tyr Arg Val Val Ser Val Leu Thr Val Leu His Gln Asp Trp Leu Asn
Gly Lys Glu Tyr Lys Cys Lys Val Ser Asn Lys Ala Leu Pro Ala Pro Ile Glu Lys Thr
Ile Ser Lys Ala Lys Gly Gln Pro Arg Glu Pro Gln Val Tyr Thr Leu Pro Pro Ser Arg
Asp Glu Leu Thr Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr Lys Thr Thr Pro
Pro Val Leu Asp Ser Asp Gly Ser Phe Phe Leu Tyr Ser Lys Leu Thr Val Asp Lys Ser
Arg Trp Gln Gln Gly Asn Val Phe Ser Cys Ser Val Met His Glu Ala Leu His Asn His
Tyr Thr Gln Lys Ser Leu Ser Leu Ser Pro Gly Lys

FIG. 5

FIG. 6 atggagacagacacactcctgctatgggtactcctgctctgggttccaggttccactggtgacttcaccccgcccaccgtgaagatcttacagtcgt
cctgcgacggcggcgggcacttcccccgaccatccagctcctgtgcctcgtctctgggtacaccccagggactatcaacatcacctggctgga
ggacgggcaggtcatggacgtggacttgtccaccgcctctaccacgcaggaggtgagctggcctccacacaaagcgagctcaccctcagcc
agaagcactggctgtcagaccgcacctacacctgccaggtcacctatcaaggtcacacctttgaggacagcaccaagaagtgtgcagattccaa
cccgagaggggtgagcgcctacctaagccggcccagcccgttcgacctgttcatccgcaagtcgcccacgatcacctgtctggtggtggacctg
gcacccagcaaggggaccgtgaacctgacctggtcccgggccagtgggaagcctgtgaaccactccaccagaaaggaggagaagcagcgc
aatggcacgttaaccgtcacgtccaccctgccggtgggcacccgagactggatcgagggggagacctaccagtgcagggtgacccaccccca
cctgcccagggccctcatgcggtccacgaccaagaccagcggcccgcgtgctgccccggaagtctatgcgtttgcgacgccggagtggccgg
ggagccgggacaagcgcaccctcgcctgcctgatccagaacttcatgcctgaggacatctcggtgcagtggctgcacaacgaggtgcagctcc
cggacgcccggcacagcacgacgcagccccgcaagaccaagggctccggcttcttcgtcttcagccgcctggaggtgaccagggccgaatg
ggagcagaaagatgagttcatctgccgtgcagtccatgaggcagcgagcccctcacagaccgtccagcgagcggtgtctgtaaatcccggtaa
agagcccaaatcttgtgacaaaactcacacatgcccaccgtgcccagcacctgaactcctggggggaccgtcagtcttcctcttccccccaaaac
ccaaggacacccctcatgatctcccggacccctgaggtcacatgcgtggtggtggacgtgagccacgaagaccctgaggtcaagttcaactggta
cgtggacggcgtggaggtgcataatgccaagacaaagccgcgggaggagcagtacaacagcacgtaccgggtggtcagcgtcctcaccgtc
ctgcaccaggactggctgaatggcaaggagtacaagtgcaaggtctccaacaaagcccctcccagcccccatcgagaaaaccatctccaaagcc
aaagggcagccccgagaaccacaggtgtacaccctgcccccatcccgggatgagctgaccaagaaccaggtcagcctgacctgcctggtcaa
aggcttctatcccagcgacatcgccgtggagtgggagagcaatgggcagccggagaacaactacaagaccacgcctcccgtgctggactccg
acggctccttcttcctctacagcaagctcaccgtggacaagagcaggtggcagcaggggaacgtcttctcatgctccgtgatgcatgaggctctg
cacaaccactacacgcagaagagcctctccctgtctccgggtaaatga

SEQUENCE LISTING

```
<160> NUMBER OF SEQ ID NOS: 2

<210> SEQ ID NO 1
<211> LENGTH: 1722
<212> TYPE: DNA
<213> ORGANISM: Artificial Sequence
<220> FEATURE:
<223> OTHER INFORMATION: Synthetic nucleotide

<400> SEQUENCE: 1
atggagacag acacactcct gctatgggta ctcctgctct gggttccagg ttccactggt      60
gacttcaccc cgcccaccgt gaagatctta cagtcgtcct gcgacggcgg cgggcacttc     120
cccccgacca tccagctcct gtgcctcgtc tctgggtaca cccagggac tatcaacatc      180 acctggctgg aggacgggca ggtcatggac gtggacttgt ccaccgcctc taccacgcag     240
gagggtgagc tggcctccac acaaagcgag ctcaccctca gccagaagca ctggctgtca     300
gaccgcacct acacctgcca ggtcacctat caaggtcaca cctttgagga cagcaccaag     360
aagtgtgcag attccaaccc gagagggtg agcgcctacc taagccggcc cagcccgttc     420
gacctgttca tccgcaagtc gcccacgatc acctgtctgg tggtggacct ggcacccagc     480
aaggggaccg tgaacctgac ctggtcccgg gccagtggga agcctgtgaa ccactccacc     540
agaaaggagg agaagcagcg caatggcacg ttaaccgtca cgtccaccct gccggtgggc     600
acccgagact ggatcgaggg ggagacctac cagtgcaggg tgacccaccc ccacctgccc     660
agggccctca tgcggtccac gaccaagacc agcgcccgc gtgctgcccc ggaagtctat     720
gcgtttgcga cgccggagtg gccggggagc cgggacaagc gcaccctcgc ctgcctgatc     780
cagaacttca tgcctgagga catctcggtg cagtggctgc acaacgaggt gcagctcccg     840
gacgcccggc acagcacgac gcagcccgc aagaccaagg gctccggctt cttcgtcttc     900
agccgcctgg aggtgaccag ggccgaatgg gagcagaaag atgagttcat ctgccgtgca     960
```

```
gtccatgagg cagcgagccc ctcacagacc gtccagcgag cggtgtctgt aaatcccggt   1020
aaagagccca atcttgtga caaaactcac acatgcccac cgtgcccagc acctgaactc    1080 ctgggggac cgtcagtctt cctcttcccc ccaaaaccca aggacaccct catgatctcc    1140
cggacccctg aggtcacatg cgtggtggtg gacgtgagcc acgaagaccc tgaggtcaag   1200
ttcaactggt acgtggacgg cgtggaggtg cataatgcca agacaaagcc gcgggaggag   1260
cagtacaaca gcacgtaccg ggtggtcagc gtcctcaccg tcctgcacca ggactggctg   1320
aatggcaagg agtacaagtg caaggtctcc aacaaagccc tcccagcccc catcgagaaa   1380
accatctcca aagccaaagg gcagccccga gaaccacagg tgtacaccct gcccccatcc   1440
cgggatgagc tgaccaagaa ccaggtcagc ctgacctgcc tggtcaaagg cttctatccc   1500
agcgacatcg ccgtggagtg ggagagcaat gggcagccgg agaacaacta caagaccacg   1560
cctcccgtgc tggactccga cggctccttc ttcctctaca gcaagctcac cgtggacaag   1620
agcaggtggc agcaggggaa cgtcttctca tgctccgtga tgcatgaggc tctgcacaac   1680
cactacacgc agaagagcct ctccctgtct ccgggtaaat ga                     1722
```

<210> SEQ ID NO 2
<211> LENGTH: 552
<212> TYPE: PRT
<213> ORGANISM: Artificial Sequence
<220> FEATURE:
<223> OTHER INFORMATION: Synthetic polypeptide

<400> SEQUENCE: 2

```
Phe Thr Pro Pro Thr Val Lys Ile Leu Gln Ser Ser Cys Asp Gly Gly
1               5                   10                  15

Gly His Phe Pro Pro Thr Ile Gln Leu Leu Cys Leu Val Ser Gly Tyr
                20                  25                  30

Thr Pro Gly Thr Ile Asn Ile Thr Trp Leu Glu Asp Gly Gln Val Met
            35                  40                  45

Asp Val Asp Leu Ser Thr Ala Ser Thr Thr Gln Glu Gly Glu Leu Ala
        50                  55                  60

Ser Thr Gln Ser Glu Leu Thr Leu Ser Gln Lys His Trp Leu Ser Asp
65                  70                  75                  80

Arg Thr Tyr Thr Cys Gln Val Thr Tyr Gln Gly His Thr Phe Glu Asp
                85                  90                  95

Ser Thr Lys Lys Cys Ala Asp Ser Asn Pro Arg Gly Val Ser Ala Tyr
                100                 105                 110

Leu Ser Arg Pro Ser Pro Phe Asp Leu Phe Ile Arg Lys Ser Pro Thr
            115                 120                 125

Ile Thr Cys Leu Val Val Asp Leu Ala Pro Ser Lys Gly Thr Val Asn
        130                 135                 140

Leu Thr Trp Ser Arg Ala Ser Gly Lys Pro Val Asn His Ser Thr Arg
145                 150                 155                 160

Lys Glu Glu Lys Gln Arg Asn Gly Thr Leu Thr Val Thr Ser Thr Leu
                165                 170                 175

Pro Val Gly Thr Arg Asp Trp Ile Glu Gly Glu Thr Tyr Gln Cys Arg
            180                 185                 190

Val Thr His Pro His Leu Pro Arg Ala Leu Met Arg Ser Thr Thr Lys
        195                 200                 205

Thr Ser Gly Pro Arg Ala Ala Pro Glu Val Tyr Ala Phe Ala Thr Pro
        210                 215                 220
```

```
Glu Trp Pro Gly Ser Arg Asp Lys Arg Thr Leu Ala Cys Leu Ile Gln
225                 230                 235                 240

Asn Phe Met Pro Glu Asp Ile Ser Val Gln Trp Leu His Asn Glu Val
                245                 250                 255

Gln Leu Pro Asp Ala Arg His Ser Thr Thr Gln Pro Arg Lys Thr Lys
            260                 265                 270

Gly Ser Gly Phe Phe Val Phe Ser Arg Leu Glu Val Thr Arg Ala Glu
        275                 280                 285

Trp Glu Gln Lys Asp Glu Phe Ile Cys Arg Ala Val His Glu Ala Ala
    290                 295                 300

Ser Pro Ser Gln Thr Val Gln Arg Ala Val Ser Val Asn Pro Gly Lys
305                 310                 315                 320

Glu Pro Lys Ser Cys Asp Lys Thr His Thr Cys Pro Pro Cys Pro Ala
                325                 330                 335

Pro Glu Leu Leu Gly Gly Pro Ser Val Phe Leu Phe Pro Pro Lys Pro
                340                 345                 350

Lys Asp Thr Leu Met Ile Ser Arg Thr Pro Glu Val Thr Cys Val Val
            355                 360                 365

Val Asp Val Ser His Glu Asp Pro Glu Val Lys Phe Asn Trp Tyr Val
    370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Lys Val Ser Asn Lys Ala
            420                 425                 430

Leu Pro Ala Pro Ile Glu Lys Thr Ile Ser Lys Ala Lys Gly Gln Pro
            435                 440                 445

Arg Glu Pro Gln Val Tyr Thr Leu Pro Pro Ser Arg Asp Glu Leu Thr
    450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Thr Thr Pro Pro Val Leu Asp Ser Asp Gly Ser Phe Phe Leu Tyr
            500                 505                 510

Ser Lys Leu Thr Val Asp Lys Ser Arg Trp Gln Gln Gly Asn Val Phe
    515                 520                 525

Ser Cys Ser Val Met His Glu Ala Leu His Asn His Tyr Thr Gln Lys
530                 535                 540

Ser Leu Ser Leu Ser Pro Gly Lys
545                 550
```

EPSIGAM FUSION PROTEIN

CROSS-REFERENCE

This application is a continuation of U.S. application Ser. No. 14/243,750, filed Apr. 2, 2014, which is incorporated by reference herein in their entirety.

Epsi-gam was made with government support under Grant No. AI092914 awarded by the National Institutes of Health. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Mar. 24, 2014, is named 36249701201SEQ.txt and is 7,463 bytes in size.

BACKGROUND OF THE INVENTION

Technical Field

The fusion protein epsi-gam provides an improved approach for the management of IgE-mediated allergic diseases and other disorders mediated through IgE receptors by crosslinking either an FcεRI or FcεRII receptor with an FcγRIIb receptor.

Asthma is a disease associated with immunoglobulin E (IgE) and IgE cell-surface receptors. The World Health Organization estimates that 235 million people worldwide suffer from the disease of Asthma. Mild to moderate asthma is typically treated with current inhaler and corticosteroid therapies, but more severe asthma is not currently well managed with current therapy modalities.

Allergic diseases are associated with IgE and IgE cell-surface receptors. Allergic disease, in general, is widely prevalent and is on the rise worldwide. Allergic diseases are often treated with vaccination, or serial small dose exposure to allergen. This therapy is however costly, time consuming, and in some cases dangerous.

BRIEF SUMMARY OF THE INVENTION

Epsi-gam is a novel fusion protein configured to cross-link either of the FcεRI or FcεRII (CD23) cell surface receptors with an FcγRIIb cell surface receptor.

FcεRI and FcγRIIb cell surface receptors are co-expressed on, for example, basophils and mast cells. The crosslinking of FcεRI and FcγRIIb receptors delivers an inhibitory signal to these cells, which inhibits their release of histamine and can provide a therapeutic effect on diseases such as asthma and allergic disease.

Basophils and mast cells are cell types that release mediators that cause asthma and allergic disease, and the cross-linking of FcεRI and FcγRIIb by epsi-gam on for example basophils and mast cells inhibits the release of histamine and other mediators responsible for the disease manifestations of asthma and allergic disease. Epsi-gam provides a therapy for asthma and allergic disease by cross-linking of FcεRI and FcγRIIb and thereby inhibiting the release of the mediators that cause asthma and allergic disease.

FcεRII and FcγRIIb are co-expressed on, for example, B lymphocytes (B-cells), and the crosslinking of FcεRII and FcγRIIb cell surface receptors on B-cells by epsi-gam inhibits the production of certain types of immunoglobulins released by the B-cells, such as IgE, thereby lowering the concentrations of IgE in circulation.

Epsi-gam further treats diseases such as asthma and allergic disease by cross-linking of FcεRII and FcγRIIb and thereby inhibiting the production of immunoglobulins, such as IgE, released by B-cells that are associated with asthma and allergic disease.

In one aspect, epsi-gam is an isolated fusion protein which comprises of an Fcε fragment functionally connected at its carboxy terminus to an Fcγ1 fragment.

In another aspect, epsi-gam is a fusion protein which comprises of the polypeptides sequence CHε2-CHε3-CHε4-γhinge-CHγ2CHγ3.

In another aspect, epsi-gam is a fusion protein that comprises of the polypeptide sequence of SEQ ID NO: 2.

In another aspect, epsi-gam is substantially encoded for by the nucleotide sequence of SEQ ID NO: 1.

In yet another aspect, epsi-gam, comprises of a homodimer of two linked polypeptides, both polypeptides comprising of the sequence of SEQ ID NO: 2.

In yet another aspect, epsi-gam comprises a heterodimer of two linked polypeptides wherein one of the linked polypeptides comprises of the sequence of SEQ ID NO: 2.

Also provided is a method for manufacturing the therapeutic fusion protein epsi-gam, comprising of synthesizing a polynucleotide that encodes epsi-gam, integrating the polynucleotide into an expression vector, transfecting a eukaryotic cell with the expression vector, and isolating the fusion protein comprising of epsi-gam.

These and other aspects will become more evident upon reference to the following detailed description and attached drawings.

BRIEF DESCRIPTION OF THE DRAWINGS

The novel features of epsi-gam are set forth with particularity in the appended claims. A better understanding of the features and advantages of epsi-gam will be obtained by reference to the following detailed description that sets forth illustrative embodiments, in which the principles of epsi-gam are utilized, and the accompanying drawings of which:

FIG. 4 is the amino acid sequence of the fusion protein epsi-gam (SEQ ID NO: 2).

FIG. 6 is an example of the nucleotide sequence of the nucleotide that substantially encodes the fusion protein epsi-gam (SEQ ID NO: 1).

DETAILED DESCRIPTION OF THE INVENTION

Unless defined otherwise, technical and scientific terms used herein have the same meaning as commonly understood by one of skill in the art.

I. Problem Solved

Fusion proteins similar to epsi-gam have shown promise for treating asthma and allergic disease in the early therapy development stage, however, these fusion molecules could not be produced in sufficient quantities to provide a practical clinical treatment regimen. The inability to produce fusion protein molecules in large quantities, or scale-up these molecules, is a problem which prevents these fusion proteins from being translated to clinical therapies. Fusion proteins similar to epsi-gam have shown to be highly prone to aggregation, which poses a risk for human clinical therapy. However, epsi-gam production results in very few protein aggregates.

Epsi-gam is unlike similar fusion protein molecules in that epsi-gam is very effectively scaled-up and thus can be feasibly translated to a viable clinical therapy. The exceptional scale-up of epsi-gam is an unexpected outcome, which allows epsi-gam to be translated into a clinical therapy. Other similar fusion molecules that cannot be scaled-up cannot be feasibly translated to a viable clinical therapy.

Therapy development typically starts with the creation and testing of a novel molecule in the laboratory, and is typically followed by the development and optimization of a scale-up procedure. The scale-up of a molecule is the production of the molecule in sufficient quantity to be useful in an application of the molecule, such as for use as a clinical therapy. The development of a scale-up procedure involves many parameters, such as the choice of a suitable expression vector, cell line and purification process. For example, the primary sequence of the protein of interest may have to be modified in order to confer the properties required for scale-up, such as high yield and low aggregation.

The development of a scale-up procedure is a complex process, and in many cases the scale-up of a particular fusion protein turns out to be unfeasible due to unforeseeable and unchangeable scale-up problems. Thus unforeseeable scale-up problems prevent the translation of molecules into a therapy for the treatment of patients, and scale-up design involves, among other steps, designing fusion proteins that will generate high yields and low aggregate levels.

Scale-up problems that are common in the development of novel protein therapies include for example high aggregation rates as well as low production yields of the protein in tissue culture.

Protein aggregation is a relatively common problem in therapeutic protein generation. However, the degree with which some proteins aggregate can render them not only difficult to manufacture, but also a clinical safety risk. Protein aggregates, should they occur on storage or after administration to the patient, can cause immunogenicity, which is an anti-drug response that can cause inactivation of the drug or other adverse clinical events.

Low yield of therapeutic recombinant proteins can render the manufacture either economically or physically unfeasible.

Fusion proteins that show promise at an early development stage may have unforeseeably high aggregation levels, low yield generation, or both high aggregation levels and low yield generation when scaled-up, rendering such fusion proteins unfeasible for translation to a clinical therapy.

Certain fusion proteins have proven to be an effective means of inhibiting IgE-mediated biological responses associated with asthma and allergic disease at the early stage of therapy development, but these molecules have failed to scale-up to sufficient quantities due to both high aggregation rates and low yield generation.

One such protein, which like epsi-gam, fuses an Fc portion of an IgE to an Fc portion of an IgG, is E2G, which is described in U.S. Pat. No. 7,488,804. Another such molecule is GE2 which, along with related molecules, is described in U.S. Pat. No. 7,265,208.

The large-scale manufacture of E2G, GE2, and related molecules were deemed unfeasible due to very high levels of aggregation during scale-up along with low yields of therapeutic protein. These scale-up problems prevented E2G, GE2, and related molecules from moving towards GMP manufacture.

Epsi-gam, however, is unlike E2G, GE2, and related molecules in that epsi-gam both produces dramatically high yields when scaled-up and has very low aggregation levels.

The exceptionally high yield of epsi-gam during scale-up is an unexpected outcome, which allows epsi-gam to be translated into a clinical therapy, while other similar fusion molecules that cannot be scaled-up cannot be feasibly translated to a viable clinical therapy.

Figure 1:
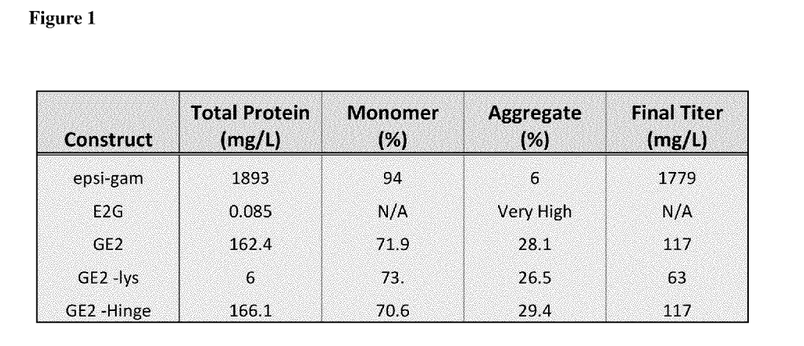
FIG. 1 is a data table of the yields of epsi-gam and similar fusion proteins produced by the described manufacturing method.

FIG. 1 is an example of a data table showing typical yields of E2G, GE2, and two other fusion proteins in the GE2 family, all generated by the substantially same manufacturing process that generated high yields of epsi-gam and that is described herein. When the yield of epsi-gam is compared with the yields of GE2, and two other fusion proteins in the GE2 family, the yield of epsi-gam is typically approximately 22-fold higher. When the yield of epsi-gam is compared to that of E2G, the yield of epsi-gam is typically a remarkable approximately 22,000-fold higher. GE2 and the two GE2 related molecules' aggregation levels were 4-5 times the aggregation levels of epsi-gam, and E2G aggregated at a substantially higher level, estimated to be as much as 10 times that of epsi-gam.

Figure 2:
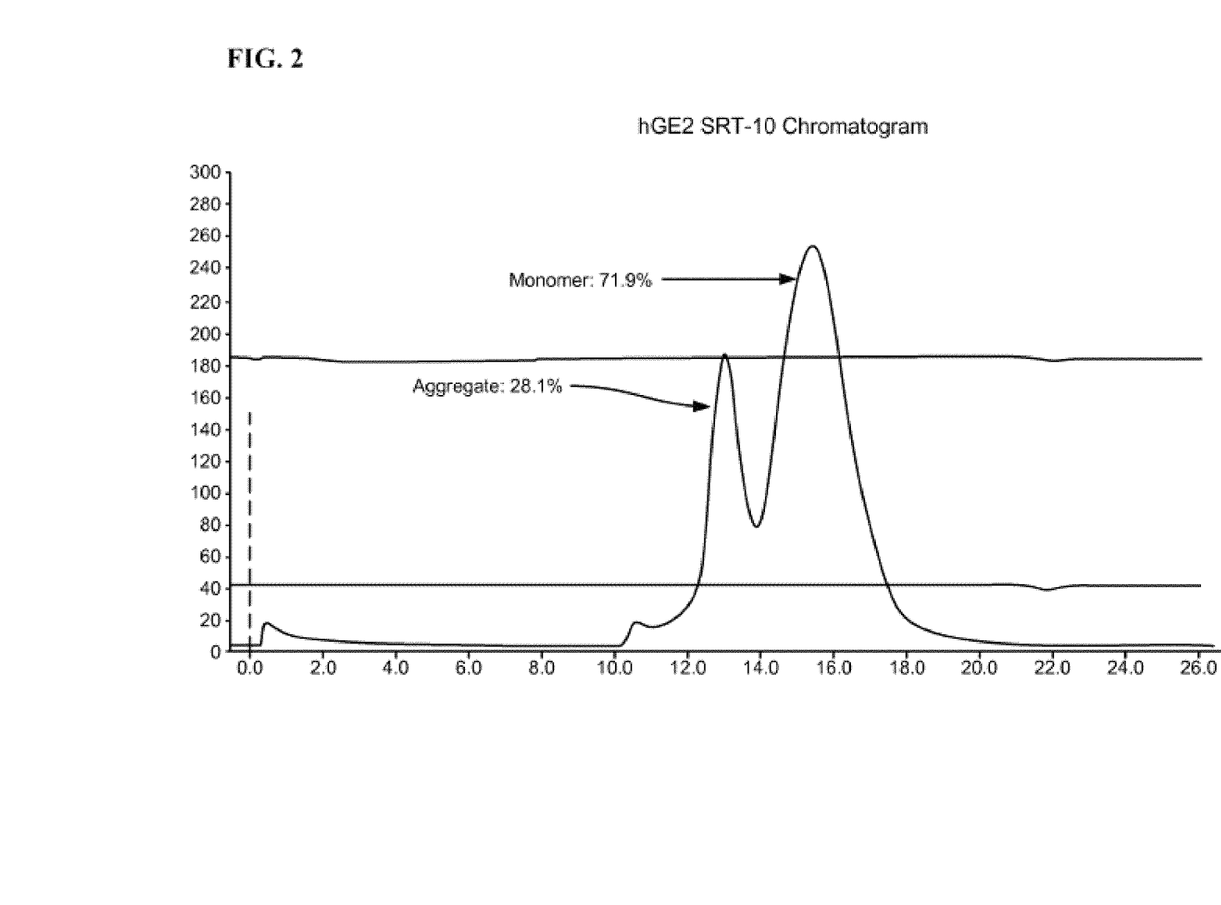
FIG. 2 is an example of a typical result of a Protein A Affinity Chromatography Assay of an expressed fusion protein similar to epsi-gam produced by the described manufacturing method.

FIG. 2 shows a typical result of a Protein A Affinity Chromatography Assay of GE2, an expressed fusion protein similar to epsi-gam produced by the manufacturing method described. As demonstrated by the chromatography result, the total aggregation of GE2 was around 28%, which is a typical result for fusion proteins similar to epsi-gam. It should be noted, however, that a more typical value for percent aggregate formation for GE2 and similar proteins might range from 30% aggregation all the way up to 60% aggregation, depending on such manufacturing factors as cells used, media type, and other related factors.

Figure 3:
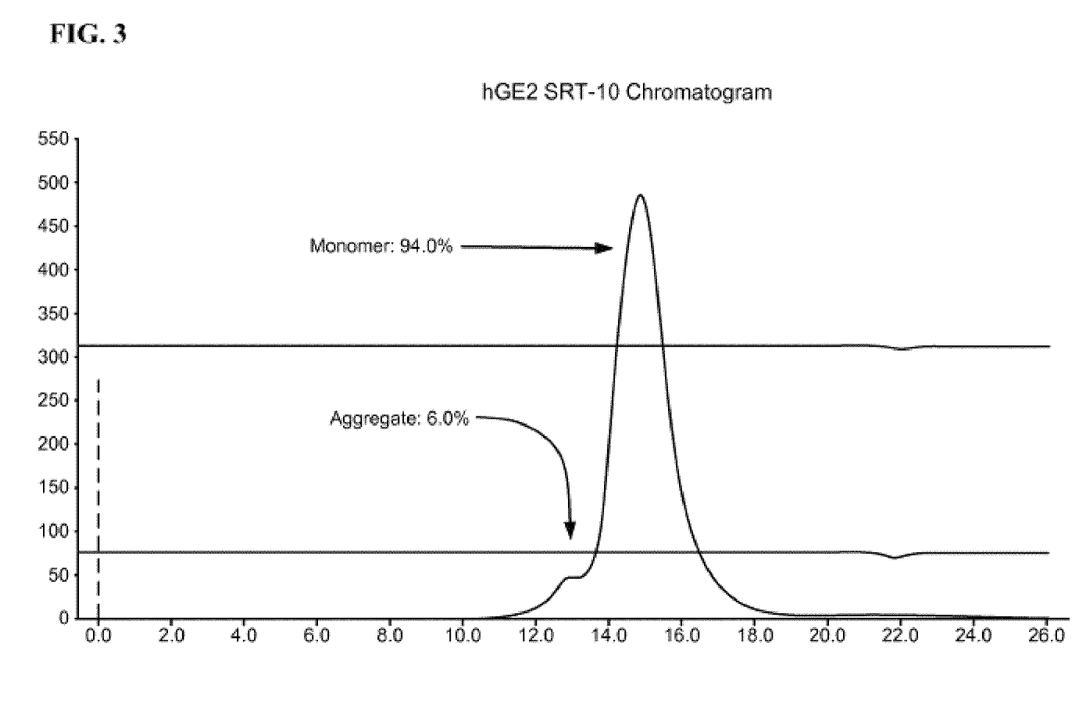
FIG. 3 is an example of a typical result of a Protein A Affinity Chromatography Assay of expressed epsi-gam produced by the described manufacturing method.

FIG. 3 shows a typical result of a Protein A Affinity Chromatography Assay of expressed epsi-gam resulting from the described manufacturing method. As demonstrated by the chromatography result, the total aggregation of epsi-gam was around a very low 6%, which is typical for epsi-gam manufacture via the method described. A typical aggregation of around 6% makes epsi-gam a highly favorable candidate for mass production and commercialization through the described manufacturing method from the standpoint of aggregation. Given the unfeasibly high aggregation results of similar fusion proteins in scale-up, the very low aggregation of epsi-gam is an unexpectedly favorable result of producing epsi-gam through the described manufacturing method.

The substantially higher yield and relatively low rate of aggregation of epsi-gam when compared to four other similar fusion proteins, including the similar E2G, was not only a substantial result, but also an unexpected one. Of five fusion molecules that have shown promise for treating asthma and allergic disease, only epsi-gam generates a substantial enough yield combined with a low enough aggregation rate to allow the novel epsi-gam fusion protein to be translated into a viable clinical therapy.

II. Definitions

The term "IgG inhibitory receptor" is used to define a member of the inhibitory receptor superfamily (IRS), now known or hereinafter discovered and includes the IgG receptor FcγRIIb. An FcγRIIb receptor cross-linked to either an FcεRI or an FcεRII receptor is capable of inhibiting an FcεR-mediated response, regardless of whether that response is mediated via IgE acting through a high-affinity IgE receptor, such as FcεRI, or a low-affinity IgE receptor, such as FcεRII, or by another mechanism such as an autoantibody to the FcεRI.

The term "FcγRIIb" is used to refer to FcγRIIb receptors of any species, including any mammalian species, as occurring in nature. In one embodiment the mammal is human.

FcγRIIb is an isoform of the low-affinity IgG receptor FcγRII containing an immunoreceptor tyrosine-based inhibition motif (ITIM). The FcγRIIb receptor is found on for example basophils, mast cells, B-cells, and dendritic cells. FcγRIIb has three alternatively spliced forms designated FcγRIIb1, FcγRIIb1', and FcγRIIb2, which differ only in their cytoplasmic domain sequences. All three alternatively spliced isoforms contain two extracellular Ig-like loops and a single conserved ITIM motif within their cytoplasmic tails, and are specifically included within the definition of FcγRIIb, along with other splice variants that might be identified in the future.

The term "FcεRI," refers to FcεRI receptors of any species, including any mammalian species that occurs in nature. FcεRI is a member of the multi-subunit immune response receptor (MIRR) family of cell surface receptors. Receptors in the MIRR family of cell surface receptors are typically capable of transducing intracellular signals through association with cytoplasmic tyrosine kinases.

The terms "FcεRII" and "CD23" are used interchangeably and refer to FcεRII receptors of any species, including any mammalian species that occur in nature.

The term "immunoglobulin" (Ig) is used to refer to the immunity-conferring portion of the globulin proteins of serum, and to other glycoproteins, which may not occur in nature but have the same functional characteristics. The term "immunoglobulin" or "Ig" specifically includes "antibodies" (Abs). While antibodies exhibit binding specificity to a specific antigen, immunoglobulins include both antibodies and other antibody-like proteins that lack antigen specificity. Native immunoglobulins are secreted by differentiated B-cells termed plasma cells, and immunoglobulins without any known antigen specificity are produced at low levels by the immune system and at increased levels by myelomas. As used herein, the terms "immunoglobulin," "Ig," and grammatical variants thereof are used to include antibodies, and Ig proteins without known antigen specificity, or without antigen binding regions.

Some of the main human antibody or immunoglobulin classes are divided into further sub-classes such as IgG. IgA, (are no subclasses of M or E that I am aware of. IgG has four known isotype subclasses: IgG1 ($\gamma_1$), IgG$_2$ ($\gamma_2$), IgG$_3$ ($\gamma_3$), and IgG$_4$ ($\gamma$4).

The constant region of an immunoglobulin heavy chain is further divided into globular, structurally discrete domains, which include heavy chain constant domains. For example, the constant region of an IgG$_1$ immunoglobulin heavy chain comprises three constant domains, CH1, CH2 and CH3, and a hinge region between the CH1 and CH2 domains. The IgE immunoglobulin heavy chain comprises four constant domains: CH1, CH2, CH3 and CH4 and does not have a hinge region.

The term "Fcγ1" refers to the Fcγ1 sequence of any species including any mammalian species, as occurring in nature. In one embodiment the animal is human.

Amino acids are represented by their common one- or three-letter codes, as is common practice in the art. Accordingly, the designations of the twenty naturally occurring amino acids are as follows: Alanine=Ala (A); Arginine=Arg (R); Aspartic Acid=Asp (D); Asparagine=Asn (N); Cysteine=Cys (C); Glutamic Acid=Glu (E); Glutamine=Gln (O); Glycine=Gly (G); Histidine=His (H); Isoleucine=Ile (I); Leucine=Leu (L); Lysine=Lys (K); Methionine=Met (M); Phenylalanine=Phe (F); Proline-Pro (P); Serine=Ser (S); Threonine=Thr (T); Tryptophan=Trp (W); Tyrosine=Tyr (Y); Valine=Val (V). The polypeptides herein include all L-amino acids, all D-amino acids or a mixture thereof. The polypeptides comprised entirely of D-amino acids are advantageous in that they are expected to be resistant to proteases naturally found within the human body, and may have longer half-lives.

A polynucleotide vector may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic proteins, conjugated with transferrin, complexed with compounds such as polyethylene glycol (PEG) to immunologically "mask" the protein and/or increase half-life, or conjugated to a non-viral protein. In one embodiment the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The term "IgE-mediated biological response" is used to refer to a condition or disease which is characterized by signal transduction through an IgE receptor, including the high-affinity IgE receptor. FcεRI, and the low-affinity IgE receptor FcεRII. The definition includes, without limitation, conditions associated with anaphylactic hypersensitivity and atopic allergies, such as, for example, asthma, allergic rhinitis, atopic dermatitis, some food allergies, chronic urticaria and angioedema, as well as the serious physiological condition of anaphylactic shock, usually caused by bee stings, severe food allergy, e.g. reactions to peanut, or medications such as penicillin.

The terms "treat" or "treatment" refer to both therapeutic treatment and prophylactic or preventative measures, wherein the object is to prevent or slow down (lessen) an undesired physiological change or disorder. Those in need of treatment include those already with the condition or disorder as well as those prone to have the condition or disorder or those in which the condition or disorder is to be prevented.

The term "patient" refers to any animal, and in one embodiment a mammal, that is the subject of an examination, treatment, analysis, test or diagnosis. In one embodiment, humans are the subject. A subject or patient may or may not have a disease or other pathological condition.

The term "disease" refers to any disruption of normal body function, or the appearance of any type of pathology.

III. Epsi-gam

FIG. 4 is the amino acid sequence of the fusion protein epsi-gam. Epsi-gam is a novel fusion protein configured to crosslink FcγRIIb cell surface receptors with either FcεRI or FcεRII cell surface receptors in order to block certain IgE-mediated biological responses.

IgE plays a key role in numerous acute and chronic allergic reactions, including for example asthma, allergic rhinitis, atopic dermatitis, severe food allergies, chronic urticaria and angioedema, as well as the serious physiological condition of anaphylactic shock as results, for example, from food allergy, bee stings, or penicillin allergy. The Fc portion of human IgE is able to bind with either FcεRI or FcεRII cell surface receptors on various cell types such as basophils, mast cells, dendritic cells, and B lymphocytes (B-cells). When antigen binds with IgE that is bound to certain cell surface receptors on for example basophils and mast cells, the IgE binding causes these cells to release vasoactive and pro-inflammatory mediators, including histamine. The mediators that are released when antigen bound IgE binds certain cell surface receptors significantly contribute to asthma as well as acute and late-phase allergic responses.

One cell surface receptor that human IgE is known to bind is the high affinity cell surface receptor known as FcεRI. FcεRI is located on cell types that include basophils and mast cells. The binding of antigen to IgE already bound to FcεRI on a cell's surface activates a cascade that leads to the release of mediators from the cell. The mediators that are released are associated with for example certain allergic diseases and asthma.

Another cell surface receptor that human IgE is known to bind with is the low affinity FcεRII receptor found on for example B-cells. The binding of IgE to B-cell surface receptors plays a role in determining the type of immunoglobulins produced by the B-cell.

The Fc portion of human IgG is known to bind with an immunoreceptor tyrosine-based inhibition motif (ITIM) containing receptor known as FcγRIIb. FcγRIIb is found on for example basophils, mast cells, dendritic cells, and B-cells. The crosslinking of the cell surface receptor FcγRIIb to the FeRI receptor inhibits release of mediators associated with certain allergic diseases and asthma.

Epsi-gam is a fusion protein comprising of an Fc portion of an IgE and an Fc portion of an IgG. Epsi-gam is configured to cross-link either of the FcεRI and FcεRII receptors with the inhibitory FcγRIIb receptor.

The cross-linking of the FcγRIIb receptor with either of the two IgE specific receptors on various cells has been found to have an overall inhibitory effect on those cells. When the FcγRIIb and FcεRI are cross-linked on the cell surfaces of either basophils or mast cells, the crosslinking causes inhibition of FcεRI mediated activation and secretion of histamine and other mediators. When FcγRIIb is cross-linked with IgE specific receptors on B-cells, the cross-linking inhibits class-switching and antigen specific IgE production.

The cross-linking of an inhibitory receptor, such as FcγRIIb, to a high-affinity IgE receptor, such as FcεRI, or a low-affinity IgE receptor, such as FcεRII, expressed on certain cells, such as mast cells basophils, and B-cells, inhibits FcεR mediated biological responses. Such biological responses include allergic reactions or autoimmune reactions via FcεR. The types of biological reactions include, without limitation, conditions associated with IgE mediated responses, such as, for example, asthma, allergic rhinitis, food allergies, chronic urticaria and angioedema, allergic reactions to hymenophthera (e.g. bee and yellow jacket) stings or medications such as penicillin up to and including the severe physiological reaction of anaphylactic shock.

Figure 5:
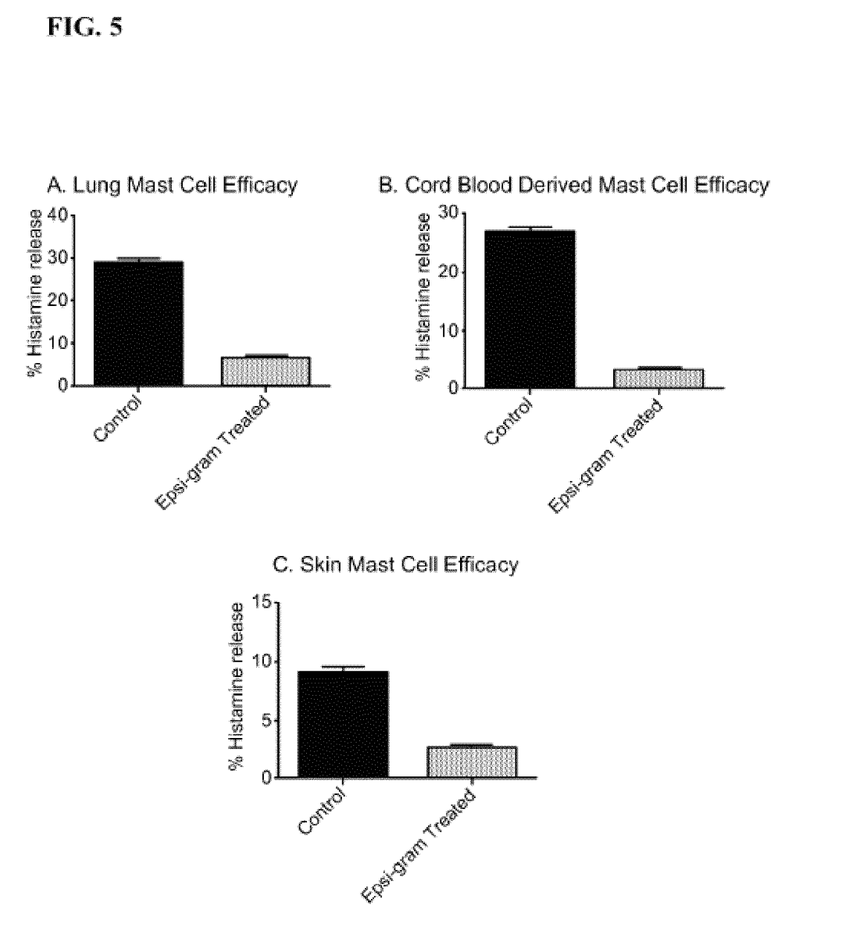
FIG. 5 is an example of a graph of typical results showing the efficacy of epsi-gam in blocking histamine release by different mast cell types.

FIG. 5 is an example of a graph of typical results showing the efficacy of epsi-gam in blocking histamine release by different mast cell types. Mast cells derived from human lung, cord blood, and skin were respectively isolated in culture and were stimulated to release histamine. As the graph shows, the cells that were treated with epsi-gam had far less release of histamine as compared to the controls. Treatment of mast cells with epsi-gam was effective in inhibiting their stimulated histamine release as compared with controls. Please also see example 1 below.

Epsi-gam is a polypeptide comprising of an Fcε fragment sequence that includes the CH2, CH3 and CH4 domains of the constant region of an IgE heavy chain (CHε2-CHε3-CHε4 sequence) linked at its C-terminus to the N-terminus of the constant region of an $IgG_1$ heavy chain that includes the functionally active hinge, CH2 and, and CH3 domains (γhinge-CHγ2-CHγ3 sequence).

The two polypeptide sequences that form epsi-gam are functionally connected, which means that they both retain the ability to bind to their respective native receptors. The receptors that epsi-gam binds to include for example, a native IgG inhibitory receptor, such as a low-affinity FcγRIIb receptor, and to either a native high-affinity IgE receptor, such as FcεRI, or a low-affinity IgE receptor, such as FcεRII. As a result, the epsi-gam fusion protein, comprising of the Fcε fragment and the Fcγ fragment functionally connected to each other, is capable of cross-linking the respective native receptors, FcγRIIb with FcεRI or FcγRIIb with FcεRII.

In order to achieve a functional connection between the two binding sequences within the epsi-gam fusion protein, it is preferred that the binding sequences retain the ability to bind to their respective corresponding receptors with a binding affinity similar to that of a native immunoglobulin ligand of that receptor. The receptor binding domains within the native IgG and IgE heavy chain constant region sequences have been identified, and it has been reported that the CH2-CH3 interface of the IgG Fc domain contains the binding sites for a number of Fc receptors, including the FcγRIIb low-affinity receptor. Based on FcεRI binding studies, six amino acid residues (Arg-408, Ser-411, Lys-415, Glu-452, Arg-465, and Met-469) located in three loops, C-D, E-F, and F-G, form the outer ridge on the most exposed side of the human IgE heavy chain CH3 domain, and are involved in binding to the high-affinity receptor FcεRI, mostly by electrostatic interactions. The high-affinity receptor binding site in the IgE protein includes the Pro343-Ser353 peptide sequence within the CH3 domain of the IgE heavy chain, but the sequences at the N-terminal or C-terminal ends of this core peptide are also necessary to provide structural scaffolding for the maintenance of a receptor binding conformation. In particular, including His, in the C-terminal region of the ε-chain makes an important contribution toward the maintenance of the high-affinity of interaction between IgE and FcεRI. The Fcε and Fcγ1 polypeptide sequences within the epsi-gam fusion protein are designed to bind to residues within such binding regions.

Epsi-gam is typically produced as and acts as either a homodimer or heterodimer, comprising of two of the fusion proteins hereinabove described covalently linked to each other.

In one embodiment, the covalent attachment of two fusion proteins that form a homodimer or heterodimer is achieved via one or more disulfide bonds. For example, the epsi-gam protein may be produced as a homodimer comprising of the two CHε2-CHε3-CHε4-$γ_1$hinge-CH$γ_1$2-CH$γ_1$3-chains connected to each other by interchain disulfide bonds, to provide an immunoglobulin-like structure. Epsi-gam may also be produced as a heterodimer, in which two different fusion proteins are linked to each other by one or more covalent linkages, such as a single or multiple disulfide bonds.

FIG. 6 is an example of the nucleotide sequence of the nucleotide that substantially encodes the fusion protein epsi-gam. Epsi-gam comprises of a nucleotide sequence that is 552 amino acids long.

The epsi-gam amino acid sequence differs from the amino acid sequence of E2G by two amino acids. The amino acids absent from epsi-gam but present in the polypeptide sequence of E2G are an Arginine and Serine located respectively at positions 321 and 322 of the E2G polypeptide sequence.

The Arginine and Serine in the polypeptide sequence of E2G, but not in the sequence of epsi-gam, are encoded by a restriction site located on the nucleotide that encodes E2G. The restriction site in the nucleotide that encodes for the Arginine and Serine found in E2G was added to the nucleotide that encodes E2G to facilitate the cloning of the nucleotide that encodes E2G.

Due at least in part to the location of the Arginine and Serine within the E2G polypeptide sequence, and the effect that these amino acids have on the conformation of E2G, E2G has high aggregation levels and low yields on scale-up.

The design of the fusion protein epsi-gam, by removal of the Arginine and Serine from positions 321 and 322 of E2G, produced unexpected and remarkable improvement with regards to both aggregation levels and yield on scale-up. As discussed above, the scale-up of epsi-gam resulted in very low aggregation rates and a 22,000-fold higher yield relative to E2G. Of the group of fusion proteins that included E2G, GE2, and similar molecules, epsi-gam is the only fusion protein that can be feasibly translated into a clinical therapy.

Epsi-gam is a novel fusion protein configured to crosslink either an FcεRI or FcεRII receptor with an FcγRIIb receptor thereby inhibiting the release of certain cellular mediators including histamine. Epsi-gam is capable of serving as a therapy for a number of human diseases including allergic reaction and asthma. Importantly, the novel fusion protein epsi-gam overcomes certain limitations presently seen in the prior art related to manufacturing that allows epsi-gam alone to be effectively translated into a usable mass produced clinical therapy.

IV. Manufacture of Epsi-gam

Epsi-gam is a fusion protein that is highly favorable for large-scale manufacture, because when epsi-gam is manufactured utilizing the described manufacturing method, epsi-gam is produced in unexpectedly high yields with a very low degree of aggregation relative to other similar fusion proteins.

Aggregated fusion protein is entirely unusable and poses a potential clinical risk. Thus a fusion protein with a high aggregation percentage cannot be transitioned to wide clinical use, whereas a fusion protein, such as epsi-gam, with an unexpectedly very low aggregation rate is highly favorable for transition to clinical use from a manufacturing stand point.

When the yield of epsi-gam produced by the described manufacturing method was compared with that of other fusion proteins produced by the same process, the yield of epsi-gam was significantly higher than that of the similar fusion proteins, and the concentration of aggregated protein was dramatically lower with epsi-gam.

Epsi-gam is a polypeptide in which the Fcε and Fcγ1 polypeptide sequences are directly fused. The nucleotide and amino acid sequences of native immunoglobulin constant regions, including native IgG and IgE constant region sequences, are available, for example, from Kabat et al., *Sequences of Proteins of Immunological Interest,* 5th Ed. Public Health Service, National Institute of Health, Bethesda, Md. (1991).

Epsi-gam is manufactured at least in part through the following generalized steps (please see example 2 below as well): Epsi-gam encoding DNA is obtained through a processes such as gene syntheses. Epsi-gam encoding cDNA is then incorporated into a suitable vector. Eukaryotic cells, such as Chinese Hamster Ovary (CHO) cells, are then transfected with the vector containing the epsi-gam encoding cDNA, through for example electroporation. Epsi-gam is then isolated from eukaryotic cells and purified.

FIG. 6 is an example of the nucleotide sequence of the nucleotide that substantially encodes the fusion protein epsi-gam. The nucleotide sequence that substantially encodes the epsi-gam polypeptide sequence can be prepared by methods well known in the art such as for example methods utilizing recombinant DNA technology or traditional gene synthesis. It should be understood that the nucleotide sequence shown in FIG. 6 is only one example of a nucleotide that encodes epsi-gam as it is well known in the art that different codons are capable of encoding the same amino acids. Thus, it is understood that certain nucleotide substitutions can be made to the nucleotide sequence shown in FIG. 6 and the nucleotide sequence will still encode epsi-gam.

Suitable vectors used in the manufacture of epsi-gam are prepared by inserting the epsi-gam encoding cDNA into a plasmid, such as the Lonza GS System, using standard techniques of recombinant DNA technology that are, for example, described in "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4 h edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991). Isolated plasmids and DNA fragments are cleaved, tailored, and ligated together in a specific order to generate the desired vectors. After ligation, the vector containing the gene to be expressed is transformed into a suitable host cell.

Host cells can be any eukaryotic or prokaryotic hosts known for expression of heterologous proteins. Accordingly, the polypeptides that comprise epsi-gam can be expressed in eukaryotic hosts, such as eukaryotic microbes (yeast) or cells isolated from multicellular organisms (mammalian cell cultures), plants and insect cells. Examples of mammalian cell lines suitable for the expression of heterologous polypeptides include monkey kidney CV1 cell line transformed by SV40 (COS-7, ATCC CRL 1651); human embryonic kidney cell line 293S (Graham et al, J. Gen. Virol. 36:59 [1977]); baby hamster kidney cells (BHK, ATCC CCL 10); Chinese hamster ovary (CHO) cells (Urlaub and Chasin, *Proc. Natl. Acad. Sci. USA* 77:4216 [1980]; monkey kidney cells (CV1-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065). In general myeloma cells, in particular those not producing any endogenous antibody, e.g. the non-immunoglobulin producing myeloma cell line SP2/0, may be used for the production of the fusion proteins herein.

*Saccharomyces cerevisiae* is the most commonly used among lower eukaryotic hosts. However, a number of other genera, species, and strains are also available and useful herein, such as *Pichia pastoris* (EP 183,070; Sreekrishna et al., *J. Basic Microbiol.* 28:165-278 (1988)). Yeast expression systems are commercially available, and can be purchased, for example, from Invitrogen (San Diego, Calif.). Other yeasts suitable for bi-functional protein expression include, without limitation, *Kluyveromyces* hosts (U.S. Pat. No. 4,943, 529), e.g. *Kluyveromyces lactis; Schizosaccharomyces pombe* (Beach and Nurse, Nature 290:140 (1981); *Aspergillus* hosts, e.g. *A. niger* (Kelly and Hynes, *EMBO J.* 4:475-479 (1985])) and *A. nidulans* (Ballance et al., *Biochem. Biophys. Res. Commun.* 112:284-289 (1983)), and *Hansenula* hosts, e.g. *Hansenula polymorpha*. Yeasts rapidly grow on inexpensive (minimal) media, the recombinant can be easily selected by complementation, expressed proteins can be specifically engineered for cytoplasmic localization or for extracellular export, and they are well suited for large-scale fermentation.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the *Bombyx mori* nuclear polyhedorsis virus which infect the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, *Drosophila melanogaster*, for which a transient or stable plasmid based transfection kit is offered commercially by Invitrogen (The DES™ System).

Prokaryotes may be hosts for the initial cloning steps, and are useful for rapid production of large amounts of DNA, for production of single-stranded DNA templates used for site-directed mutagenesis, for screening many mutants simultaneously, and for DNA sequencing of the mutants generated. *E. coli* strains suitable for the production of the peptides of epsi-gam include, for example, BL21 carrying an inducible 17 RNA polymerase gene (Studier et al., *Methods Enzymol.* 185:60-98 (1990)); AD494 (DE3); EB 105; and CB (*E. coli* B) and their derivatives; K12 strain 214 (ATCC 31,446); W3110 (ATCC 27.325); X1776 (ATCC 31,537); HB101 (ATCC 33.694); JM101 (ATCC 33,876); NM522 (ATCC 47,000); NM538 (ATCC 35,638); NM539 (ATCC 35,639), etc. Many other species and genera of prokaryotes may be used as well. The peptide of the present epsi-gam can be readily produced in large amounts by utilizing recombinant protein expression in bacteria, where the peptide is fused to a cleavable ligand used for affinity purification.

Suitable promoters, vectors and other components for expression in various host cells are well known in the art.

Transfection of a suitable cell with the vector containing the nucleotide sequence that encodes epsi-gam is achieved for example utilizing the technique of electroporation.

Whether a particular cell or cell line is suitable for the production of the polypeptides herein in a functionally active form, can be determined by empirical analysis. For example, an expression construct comprising the coding sequence of the desired protein may be used to transfect a candidate cell line. The transfected cells are then grown in culture. The transfected cells secrete epsi-gam into the cell medium.

Isolation of the fusion protein epsi-gam may be achieved by for example collecting the medium in which the transfected cells are grown, assaying for the presence of secreted epsi-gam, and purifying the secreted epsi-gam. Epsi-gam can then be quantitated by methods known in the art, such as by ELISA with an antibody specifically binding the IgG, IgE portion of the protein.

V. Nature of the Diseases Targeted

Allergic reactions are classified depending on the type of immune response induced and the resulting tissue damage that develops as a result of reactivity to an antigen. A Type I reaction (immediate hypersensitivity) occurs when an antigen (called an allergen in this case) entering the body encounters mast cells or basophils which are sensitized as a result of IgE to that antigen being attached to their high-affinity receptors, FcεRI. Upon reaching the sensitized mast cell, the allergen cross-links IgE bound to FcεRI, causing an increase in intracellular calcium ($Ca^{2+}$) that triggers the release of pre-formed mediators, such as histamine and proteases, and newly synthesized, lipid-derived mediators such as leukotrienes and prostaglandins. These autocoids produce the acute clinical symptoms of immediate hypersensitivity allergy. The stimulated basophils and mast cells will also produce and release proinflammatory mediators, which participate in the acute and delayed phase of allergic reactions.

A large variety of allergens have been identified so far, and new allergens are regularly identified, cloned and sequenced. Allergens enter the body in different forms and are associated with different diseases and disease processes.

Inhalation of airborne allergens results in allergic rhinitis and allergic asthma, which can be acute or chronic depending on the nature of the exposure(s). Exposure to airborne allergens in the eye results in allergic conjunctivitis. Common airborne allergens includes pollens, animal danders, dust mites and other insect proteins and mold spores that comprise the most frequent cause of seasonal hay fever and allergic asthma.

Ingestion of an allergen results in gastrointestinal and systemic allergic reactions. The most common food allergens involved are peanuts, shellfish, milk, fish, soy, wheat, egg and tree nuts such as walnuts. In susceptible people, these foods can trigger a variety of allergic symptoms, such as nausea, vomiting, diarrhea, urticaria, angioedema, asthma and full-blown anaphylaxis.

Cutaneous exposure to an allergen, such as natural rubber latex proteins as found in latex gloves, may result in local allergic reactions manifest as hives (urticaria) at the places of contact with the allergen.

Systemic exposure to an allergen such as occurs with a bee sting, the injection of penicillin, or the use of natural rubber latex (NRL) gloves inside a patient during surgery may result in, cutaneous, gastrointestinal and respiratory reactions up to and including airway obstruction and full blown anaphylaxis. Hymenoptera stings are insects that commonly cause allergic reactions, often leading the anaphylactic shock. Examples include various bees including honeybees, yellow jackets, yellow hornets, wasps and white-faced hornets. Certain ants known as fire ants (*Solenopsis invicta*) are an increasing cause of allergy in the US as they expand their range in this country. Proteins in NRL gloves have become an increasing concern to health care workers and patients and at present, there is no successful form of therapy for this problem except avoidance.

VI. Therapeutic Uses of Epsi-gam

Epsi-gam provides a new therapeutic strategy for treating diseases mediated through the high-affinity IgE receptor.

In particular, epsi-gam provides compounds for use in the treatment and prevention of for example include but are not limited to asthma, allergic rhinitis, atopic dermatitis, severe food allergies, chronic urticaria and angioedema, as well as the serious physiological condition of anaphylactic shock as results, for example, from bee stings or penicillin allergy.

Epsi-gam can be further used to acutely or chronically inhibit IgE mediated reaction to major environmental and occupational allergens.

Epsi-gam can be used to provide protection for allergy vaccination or immunotherapy, inducing a state of non-allergic reactivity during treatment for specific allergens.

Epsi-gam can also have a prophylactic effect against allergic disease by preventing allergic sensitization to environmental and occupational allergens when administered to at-risk individuals. For example, those at genetic risk of asthma and those exposed to occupational allergens in the workplace.

Epsi-gam can be used acutely to desensitize a patient so that the administration of a therapeutic agent, such as penicillin, can be given safely. Similarly, epsi-gam can be used to desensitize a patient so that standard allergen vaccination may be given with greater safety.

Epsi-gam can also be used as chronic therapy to prevent clinical reactivity to prevent environmental allergens such as foods or inhalant allergens.

In addition, epsi-gam holds great promise for the treatment of chronic urticaria and angioedema. Chronic urticaria and angioedema often occur together although they occur individually as well. These conditions are common and once present for more than six months, they often last a decade or more. Epsi-gam is believed to form the basis for a novel and effective treatment of these diseases by safely blocking access to the FcεRI.

In addition epsi-gam may be used for the treatment of inflammatory arthritis, such as rheumatoid arthritis or other autoimmune conditions depending on the role of mast cells and basophils in those diseases.

VII. Compositions and Formulations

For therapeutic uses, including prevention, epsi-gam can be formulated as a pharmaceutical composition in admixture with pharmaceutically acceptable carriers or diluents. Methods for making pharmaceutical formulations are well known in the art.

Pharmaceutical compositions of epsi-gam can comprise a fusion molecule along with conventional carriers and optionally other ingredients.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents.

The compositions or pharmaceutical compositions can be administered by different routes including, but not limited to, oral, intravenous, intra-arterial, intraperitoneal, subcutaneous, intranasal or intrapulmonary routes.

Systemic administration can also be by transmucosal or transdermal. For transmucosal or transdermal administration, penetrants appropriate to the barrier to be permeated are used in the formulation.

One route for administration of the compounds of the invention may be inhalation for intranasal and/or intrapulmonary delivery. One example of a method of intrapulmonary delivery is the breath actuated metered dose inhaler that operates to provide automatically a metered dose in response to the patient's inspiratory effort.

For topical administration, the compounds of the invention are formulated into ointments, salves, gels, or creams, as is generally known in the art.

The compounds of the present invention may be administered in combination with one or more further therapeutic agents for the treatment of IgE-mediated allergic diseases or conditions. Such further therapeutic agents include, without limitation, corticosteroids, beta-antagonists, theophylline, leukotriene inhibitors, allergen vaccination, and biologic response modifiers such as soluble recombinant human soluble IL-4 receptors (Immunogen), and therapies that target Toll-like receptors. (see, e.g. Barnes, *The New England Journal of Medicine* 341:2006-2008 (1999)). Thus the compounds of the present invention can be used to supplement traditional allergy therapy, such as corticosteroid therapy performed with inhaled or oral corticosteroids.

VIII. Articles of Manufacture

The invention also provides articles of manufacture comprising epsi-gam. The article of manufacture comprises a container and a label or package insert on or associated with the container.

Suitable containers include, for example, bottles, vials, syringes, etc. The containers may be formed from a variety of materials such as glass or plastic.

The container holds a composition which is effective for treating the condition and may have a sterile access port.

The container may also be an inhalation device such as those discussed above.

At least one active agent in the composition is epsi-gam.

The label or package insert indicates that the composition is used for treating the condition of choice, such as an allergic condition, such as asthma or any of the IgE-mediated allergies discussed above.

Further details are illustrated by the following non-limiting Examples section.

EXAMPLES

Example 1

Mast Cell Efficacy

The following provides an example of how mast cell efficacy results are obtained.

Mast cells are sensitized by incubation with allergic human serum as the source of allergen-specific IgE, for 3-5 days, at 37 C in 5% $CO_2$.

After this time, cells are exposed to epsi-gam for 2 hours typically, but possibly as long as 24 hours, after which time, cells are exposed to allergen for 45 min, to allow for histamine degranulation.

The histamine released into the supernatant is collected, as are the cells, and histamine levels are quantified using a histamine EIA.

Example 2

Manufacture of Epsi-gam

The following provides an example of how epsi-gam was manufactured.

The nucleotide sequence of SEQ ID NO: 1, which substantially codes for the amino acid sequence of epsi-gam was generated through gene synthesis. Following gene synthesis the sequence was inserted into the cloning vector pUC57. Restriction sites were created on either side of the expression cassette, in order to be able to excise this gene for cloning into an expression vector.

The cloning vector containing epsi-gam was further digested with HindIII and EcoRI restriction enzymes for cloning into an expression vector such as the Lonza GS System pXC-17.4 plasmid for the expression of single subunit proteins. This expression plasmid links the expression of an exogenous protein to the glutamine synthetase (GS) gene.

The GS Chinese Hamster Ovary (CHO) cell lines have mutations in both copies of the GS gene, so that they require the expression of GS on the expression plasmid for survival in the absence of glutamine, an amino acid that is essential for growth.

Once the epsi-gam insert was cloned into this vector, individual bacterial colonies were selected for sequence analysis. The plasmids are verified for proper sequence and proper orientation within the plasmid using primers that are situated outside the ORF of epsi-gam. Based on this information, one single clone is selected for scale-up and generation of a sufficient quantity of plasmid for transfection of CHO cells.

The bacterial colony was grown in animal component free, soy tryptone based, media, and the plasmid was purified using a low endotoxin kit.

GS CHO cells were thawed into appropriate media formulation under no selection; ie containing L-glutamine. CHO cells were maintained at 5% CO2 in a 37 C incubator.

Transfection of CHO cells with the expression vector was performed using electroporation. Cells were electroporated by delivering a single pulse of 300V, 900 uF with resistance set to infinity. Immediately after electroporation, each batch of cells was added to a flask containing the appropriate media. Cells were gently mixed and incubated overnight in a cell culture incubator. The next day, cells were centrifuged to remove media containing plasmid.

When cell numbers reach about 0.6×106 cells per mL, cells were expanded into selection media. After two weeks in selection, individual colonies of CHO cells were selected based on growth on transwell plates. CHO cells secreted the fusion protein having the sequence of SEQ ID NO: 2.

Individual colonies were assessed based on growth and productivity characteristics, through scale-up.

The quantity and integrity of product was then assayed by protein A affinity chromatography, followed by AU280 nm; ELISA and SDS-PAGE analysis.

What is claimed is:

1. A method for manufacturing a pharmaceutical composition comprising a fusion protein comprising the sequence of SEQ ID NO:2, said method comprising
synthesizing said fusion protein; and
isolating said fusion protein, wherein said fusion protein aggregates at a rate of 6% or less.

2. The method of claim 1, further comprising combining said fusion protein with an excipient or carrier.

3. The method of claim 2, wherein said excipient and said carrier comprise one or more of calcium carbonate, calcium phosphate, lactose, glucose, a starch, gelatin, a vegetable oil, and a polyethylene glycol containing compound.

4. The method of claim 1, further comprising combining said fusion protein with a therapeutic agent.

5. The method of claim 4, wherein said therapeutic agent comprises one or more of a corticosteroid, a beta-antagonist, a theophylline, a leukotriene inhibitor, and an allergen vaccination.

6. The method of claim 1, further comprising packaging said fusion protein in a container having a label, said label indicating that said fusion protein is used for treating an allergic condition.

7. A method for providing a first therapeutic agent to a subject, wherein said subject has had an allergic reaction to said first therapeutic agent in the past or said first therapeutic agent is expected to produce an allergic reaction in said subject, said method comprising provide to said subject a fusion protein comprising of the sequence of SEQ ID NO:2 thus desensitizing said subject; and providing to said subject said first therapeutic agent.

8. The method of claim 7, wherein said fusion protein is provided before said therapeutic agent is provided.

9. The method of claim 7, wherein said therapeutic agent is penicillin or said therapeutic agent is a member of the penicillin family.

10. The method of claim 7, wherein said therapeutic agent is an allergen vaccine.

11. The method of claim 7, wherein said fusion protein is provided to said subject subcutaneously.

12. The method of claim 7, wherein said fusion protein is provided to said subject together with an excipient or carrier.

13. The method of claim 12, wherein said excipient and said carrier comprise one or more of calcium carbonate, calcium phosphate, lactose, glucose, a starch, gelatin, a vegetable oil, and a polyethylene glycol containing compound.

14. The method of claim 7, wherein said fusion protein is provided to said subject together with a second therapeutic agent.

15. The method of claim 14, wherein said second therapeutic agent comprises one or more of a corticosteroid, a beta-antagonist, a theophylline, a leukotriene inhibitor, and an allergen vaccination.

\* \* \* \* \*